United States Patent [19]

Pahade et al.

[11] Patent Number: 4,664,686
[45] Date of Patent: May 12, 1987

[54] PROCESS TO SEPARATE NITROGEN AND METHANE

[75] Inventors: Ravindra F. Pahade, North Tonawanda; James J. Maloney, Tonawanda; James R. Handley, Amherst, all of N.Y.

[73] Assignee: Union Carbide Corporation, Danbury, Conn.

[21] Appl. No.: 827,165

[22] Filed: Feb. 7, 1986

[51] Int. Cl.[4] .................................................. F25J 3/02
[52] U.S. Cl. ........................................... 62/24; 62/28; 62/31; 62/36; 62/42
[58] Field of Search ................... 62/24, 28, 31, 36, 42

[56] References Cited

U.S. PATENT DOCUMENTS

| | | | |
|---|---|---|---|
| 3,592,015 | 7/1971 | Streich et al. | 62/24 |
| 3,747,359 | 7/1973 | Streich | 62/24 |
| 4,311,496 | 1/1982 | Fabian | 62/17 |
| 4,338,107 | 7/1982 | Swallow | 62/24 |
| 4,352,685 | 10/1982 | Swallow | 62/28 |
| 4,415,345 | 11/1983 | Swallow | 62/28 |
| 4,451,275 | 5/1984 | Vines et al. | 62/28 |
| 4,479,871 | 10/1984 | Pahade et al. | 208/340 |
| 4,501,600 | 2/1985 | Pahade | 62/28 |

Primary Examiner—Ronald C. Capossela
Attorney, Agent, or Firm—Stanley Ktorides

[57] ABSTRACT

A process for more efficiently separating nitrogen and methane using a double column cryogenic rectification nitrogen rejection unit wherein feed is passed through a high pressure stripping column prior to the nitrogen rejection unit. As a result, higher pressure methane can be recovered with reduced compression requirements, and an upgraded feed to the nitrogen rejection unit enables more efficient separation.

18 Claims, 3 Drawing Figures

PROCESS TO SEPARATE NITROGEN AND METHANE

TECHNICAL FIELD

This invention relates to the separation of nitrogen from methane employing cryogenic rectification using a double column arrangement and is an improvement whereby some methane may be recovered at a pressure which exceeds that of the methane from the rectification and whereby the rectification can operate at higher efficiency especially at lower nitrogen concentrations in the feed.

BACKGROUND ART

A problem often encountered in the production of natural gas from underground reservoirs is nitrogen contamination. The nitrogen may be naturally occurring and/or may have been injected into the reservoirs as part of an enhanced oil recovery (EOR) or enhanced gas recovery (EGR) operation.

One conventional method of removing the nitrogen contaminant from the natural gas is to pass a stream containing nitrogen and methane to a nitrogen rejection unit (NRU) comprising double cryogenic rectification columns wherein the nitrogen and methane are separated.

Although this conventional method for separating nitrogen and methane has worked reasonably well, two possible problems, both related to the nature of rectification, have heretofore acted as a detriment to the efficiency of the method.

One problem relates to the fact that rectification relies on mass transfer of components in different concentrations in countercurrent liquid-vapor flow. The efficiency of such mass transfer is hindered by higher pressures and thus the rectification is best conducted at low pressures consistent with required concentration driving forces and temperature considerations well known to those skilled in the art. Such lower pressure rectification produces methane at the low pressure. Although the methane product from the low pressure column is liquid pumped to a higher pressure prior to rewarming, that pumping is limited by process refrigeration requirements. Typically, the methane product pressure level as it emerges from the double column NRU is considerably lower than the feed pressure level. Since it is often desired to have product methane at higher pressure, for example for introduction into a high pressure natural gas pipeline, the methane product must be compressed to a higher pressure than that at which it is when it emerges from the double column NRU. This compression involves considerable expense. It is therefore desirable to have a nitrogen-methane separation process employing cryogenic rectification wherein some methane product can be produced at a pressure which exceeds that of the methane as it emerges from the double column NRU, consequently reducing the amount of methane compression required.

Another problem relates to the fact that the efficiency of the double column cryogenic rectification is hindered at low concentrations of the more volatile component as this reduces the quality of the available reflux for the top of the low pressure column. In the case of a nitrogen methane mixture, the efficiency of the NRU is significantly reduced when the NRU feed has a nitrogen concentration of less than about 35 mole percent. This problem has been addressed by recycling a portion of the nitrogen stream from the NRU separation back to the natural gas feed stream, thus keeping the nitrogen concentration high enough for effective separation. However, this method has two disadvantages. First, use of a nitrogen recycle in this manner increases the NRU plant size requirements. Second, this process leads to significantly increased power requirements, since relatively pure nitrogen from the exit stream must be separated over again from the natural gas feed.

A recent significant advancement in a double-column NRU process is described in U.S. Pat. No. 4,415,345 -Swallow. In this process, a portion of the product nitrogen stream from the low pressure column is rewarmed to ambient temperature, compressed to the pressure level of the high pressure column, and then cooled against the rewarming low pressure nitrogen. This nitrogen stream is then condensed in the low pressure column reboiler along with the nitrogen vapor from the high pressure column. By supplementing the amount of nitrogen condensed in this manner, which is often referred to as a nitrogen heat pump, additional nitrogen reflux is available to the low pressure column, thereby permitting a higher percentage recovery of inlet methane. This process has the advantage over the previous state of the art in that a reduction in capital and operating costs is achieved. However, process equipment such as distillation columns and heat exchangers must still be sized for the additional recirculation of nitrogen and a separate nitrogen gas compressor is still required. It is therefore desirable to have a nitrogen-methane separation process employing double column cryogenic rectification which can operate more efficiently at lower available nitrogen concentrations without the need for nitrogen recycle or a nitrogen heat pump.

Another problem often encountered in the cryogenic separation of nitrogen and methane in a stream from a natural gas reservoir is a high concentration of carbon dioxide in the nitrogen-methane feed. Since carbon dioxide freezes at a relatively high temperature, carbon dioxide must be removed from the feed prior to cryogenic processing so as to be at a level which does not exceed solubility limits. As can be appreciated the higher is the concentration of carbon dioxide in the original feed, the more expensive, from both a capital and operating cost standpoint, is the carbon dioxide removal step. It would therefore be desirable to have a nitrogen methane separation process which can tolerate a significantly higher carbon dioxide concentration in the nitrogen-methane feed without the need for extensive and expensive carbon dioxide removal steps.

It is therefore an object of this invention to provide an improved process for separating nitrogen and methane.

It is a further object of this invention to provide an improved process for separating nitrogen and methane employing double column cryogenic rectification in a nitrogen rejection unit which can operate more efficiently at lower available nitrogen concentrations and which can produce some methane at a pressure which exceeds that of the methane as it emerges from the nitrogen rejection unit.

SUMMARY OF THE INVENTION

The above and other objects which will become apparent to one skilled in the art upon a reading of this disclosure are attained by this invention which is:

A process for the separation of nitrogen and methane employing double column cryogenic rectification in a nitrogen rejection unit comprising the recovery of methane at a pressure which exceeds that of methane as it emerges from the nitrogen rejection unit by the steps of:

(a) introducing feed containing nitrogen and methane into a high pressure stripping column operating at a pressure in the range of from 200 to 600 psia;

(b) passing feed down the stripping column against upflowing vapor to produce stripping column bottom liquid having a methane concentration which exceeds that of the feed, and stripping column top vapor having a nitrogen concentration which exceeds that of the feed;

(c) partially vaporizing bottom liquid to produce nitrogen-richer vapor and methane-richer fluid;

(d) employing nitrogen-richer vapor in the stripping column as upflowing vapor;

(e) passing at least some of the stripping column top vapor to a nitrogen rejection unit for separation by double column cryogenic rectification into nitrogen-richer and methane-richer fractions; and (f) recovering methane-richer fluid at a pressure which exceeds that of the methane-richer fraction as it emerges from the double column nitrogen rejection unit.

The term "column" is used herein to mean a distillation, rectification or fractionation column, i.e., a contacting column or zone wherein liquid and vapor phases are countercurrently contacted to effect separation of a fluid mixture, as for example, by contacting of the vapor and liquid phases on a series of vertically spaced trays or plates mounted within the column or alternatively, on packing elements with which the column is filled. For an expanded discussion of fractionation columns see the Chemical Engineer's Handbook, Fifth Edition, edited by R. H. Perry and C. H. Chilton, McGraw Hill Book Company, New York Section 13, "Distillation" B. D. Smith et al, page 13-3, *The Continuous Distillation Process.*

The term "double column", is used herein to mean a high pressure column having its upper end in heat exchange relation with the lower end of a low pressure column. An expanded discussion of double columns appears in Ruheman, "The Separation of Gases" Oxford University Press, 1949, Chapter VII, Commercial Air Separation, and Barron, "Cryogenic Systems", McGraw-Hill, Inc., 1966, p. 230, *Air Separation Systems.*

The term "stripping column" is used herein to mean a column where the feed is introduced to the top of the column and the more volatile components are removed or stripped from descending liquid by rising vapor.

The terms "nitrogen rejection unit" and "NRU" are used herein to mean a facility wherein nitrogen and methane are separated by cryogenic rectification, comprising a double column and the attendant interconnecting equipment such as liquid pumps, phase separators, piping, valves and heat exchangers.

The term "indirect heat exchange" is used herein to mean the bringing of two fluid streams into heat exchange relation without any physical contact or intermixing of the fluids with each other.

DETAILED DESCRIPTION

The invention will be described in detail with reference to the drawings.

Figure 1:
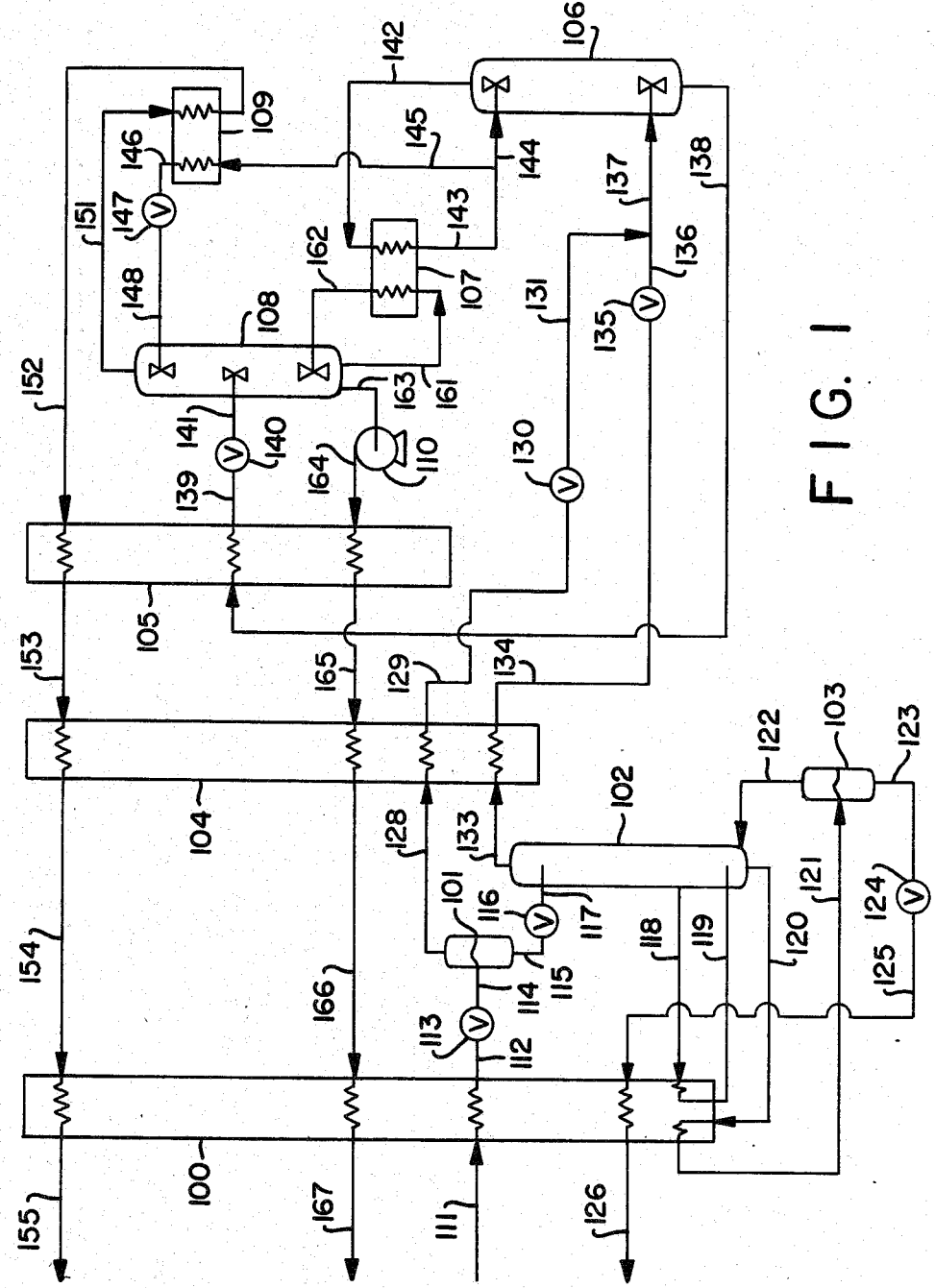
FIG. 1 is a schematic flow diagram of one preferred embodiment of the nitrogen and methane separation process of this invention.

Referring now to FIG. 1, feed stream 111 is cooled by indirect heat exchange with return streams by passage through heat exchanger 100 and the cooled feed 112 is reduced in pressure by passage through valve 113 and passed as stream 114 to phase separator 101. Feed 111 contains nitrogen and methane and may also contain a number of other species which normally occur in natural gas reservoirs such as carbon dioxide and higher hydrocarbons having two to four carbon atoms. Generally this stream will have been pretreated in order to remove to the extent practical higher hydrocarbons and natural gas liquids. The nitrogen concentration in feed 111 may be as low as 5 percent or as high as 80 percent. Feed 111 may have a pressure in the range of from 200 to 2000 psia, but preferably has a pressure in the range of from 500 to 1000 psia. Generally feed 111 is in the vapor phase and is partly liquefied when it is cooled 112. Following expansion through valve 113, some of the liquid would be vaporized due to the lower pressure level but the remaining liquid would be somewhat enriched in methane. Vapor from phase separator 101 is passed as stream 128 through heat exchanger 104 where it is cooled by indirect heat exchange with return streams; the cooled stream 129 is reduced in pressure by passage through valve 130 and passed 131 into the NRU. FIG. 1 illustrates the embodiment wherein stream 131 is combined with stripping column 102 top vapor 133 and the combined stream 137 introduced into the NRU.

Liquid 115 from phase separator 101 is reduced in pressure by passage through valve 116 and the resulting two-phase stream 117 is introduced as feed into stripping column 102.

Stripping column 102 operates at a high pressure which is in the range of from about 200 psia to 600 psia. The operating pressure of the stripping column within this range is determined, in part, by the pressure available in the feed.

In the stripping column, liquid is passed down against upflowing vapor to produce a top vapor having a nitrogen concentration exceeding that of the feed and a bottom liquid having a methane concentration exceeding that of the feed. FIG. 1 illustrates stripping column reboil from two sources. One source comprises removal of a liquid stream 118 from the stripping column, partial vaporization of the stream by cold end partial traverse of heat exchanger 100 and return of the resulting stream 119 to the column. Since this boiling is done at a colder location in the column, this permits cooling of the feed stream to a lower temperature. Another source of reboil comprises removal of stripping column bottom liquid as stream 120, partial vaporization of this stream by warm end partial traverse of heat exchanger 100 to produce nitrogen-richer vapor and methane-richer fluid, and introduction of the resulting stream 121 to phase separator 103 from which nitrogen-richer vapor 122 is passed into stripping column 102 as upflowing vapor.

Methane-richer fluid is recovered as product methane at a pressure which exceeds that of methane as it emerges from the double-column NRU. In this way methane is produced at a higher pressure, without additional compression, than that possible from the NRU, resulting in reduced overall compression requirements which translates into reduced capital and operating costs. FIG. 1 illustrates the embodiment wherein methane-richer fluid 123 from phase separation 103 is reduced in pressure by passage through valve 124 and the resulting stream 125 is warmed by passage through heat exchanger 100 and recovered as high pressure methane gas 126. Generally the pressure of methane-richer fluid 126 recovered from the stripping column will exceed that of methane 167 as it emerges from the NRU. The pressure of the methane product from the stripping column will be a function of feed pressure and feed composition, and generally will be at least 1.5 times the NRU methane pressure and often will be at least 2.0 times the NRU methane pressure. Generally the stripping column will enable recovery of from about 20 to as much as 90 percent of the methane in the stripping column feed as higher pressure methane-richer fluid.

Stripping column top vapor 133 is partially condensed by passage through heat exchanger 104 against returning streams and resulting stream 134 is reduced in pressure by passage through valve 134 and passed 136 into the NRU. As indicated previously, FIG. 1 illustrates the embodiment wherein the top vapor (which is now a two-phase stream) is combined with stream 131 and the combined stream 137 introduced into the NRU. Because the feed to the NRU, which in FIG. 1 is stream 137, contains a higher concentration of nitrogen than would otherwise have been the case, the NRU can generate higher quality nitrogen reflux and thus recover a higher fraction of the methane in the NRU feed without the need for nitrogen product recirculation or a nitrogen heat pump. It should be noted that this system has the advantage of allowing higher pressure methane recovery over the entire feed composition range of from 5 to 80 percent nitrogen. However, the advantage of improved NRU column reflux is attained primarily at the feed composition range of 5 to 35 percent nitrogen. Thus, the process of this invention has dual benefits at the lower nitrogen feed composition range of 5 to 35 percent.

In the embodiment illustrated in FIG. 1, the NRU is a double column comprising high pressure column 106 and low pressure column 108 in heat exchange relation through heat exchanger 107. A double column is the preferred NRU for the process of this invention.

Referring back to FIG. 1, feed containing methane and nitrogen is introduced into high pressure column 106, which is operating at a pressure in the range of from 200 to 450 psia, and wherein the feed is separated into nitrogen-enriched vapor and methane-enriched liquid. Methane-enriched liquid is passed 138 through heat exchanger 105 where it is subcooled by indirect heat exchange with return streams. The resulting stream 139 is reduced in pressure by passage through valve 140 and then passed as feed stream 141 into low pressure column 108. Within low pressure column 108, which is operating at a pressure in the range of from 15 to 45 psia, the feed is separated into nitrogen-richer and methane-richer fractions. The nitrogen-enriched vapor from the high pressure column is condensed by passage through heat exchanger 107 to form stream 143, and a portion 144 is returned to the high pressure column as reflux. Another portion 145 is subcooled by passage through heat exchanger 109 and the resulting stream 146 is reduced in pressure by passage through valve 147 and passed 148 into low pressure column 108 as reflux. Reboiler duty for low pressure column 108 is provided by withdrawal of liquid bottoms stream 161 and partial vaporization of this stream by passage through heat exchanger 107 to form two-phase stream 162 which is returned to the column. The vapor portion provides vapor upflow for the low pressure column while the liquid portion forms the methane-richer fraction which is withdrawn from the NRU as stream 163 at a pressure corresponding to that of the low pressure column.

The methane-richer fraction is increased in pressure over the pressure which it has when it emerges from the low pressure column 108 by passage through pump 110. Pressurized return stream 164 is then warmed by passage through heat exchanger 105 and passed 165 through heat exchanger 104 wherein it boils to sustain the cooling and condensation of streams 128 and 133. The resulting stream 166 is further warmed by passage through heat exchanger 100 and the resulting stream recovered as low pressure methane gas 167 emerging from the NRU.

The nitrogen-richer fraction from the low pressure column is taken from the column as stream 151 and warmed by passage through heat exchanger 109 to form stream 152. This stream is successively warmed by passage through heat exchanger 105 to form stream 153, passage through heat exchanger 104 to form stream 154, and passage through heat exchanger 100 to form stream 155 which may be recovered in whole or in part or simply released to the atmosphere.

Figure 2:
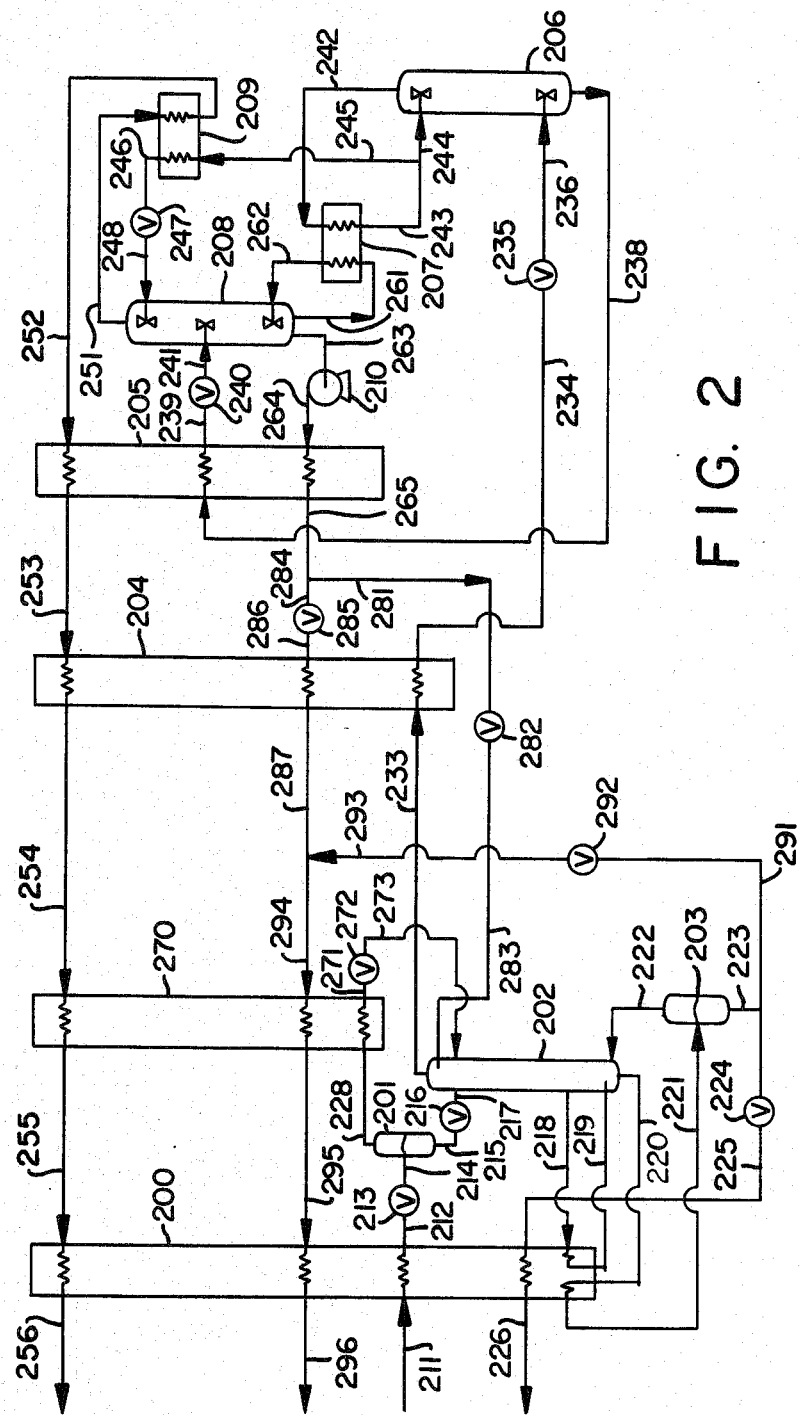
FIG. 2 is a schematic flow diagram of another preferred embodiment of the nitrogen and methane separation process of this invention wherein some methane from the NRU is employed as wash liquid in the stripping column.

Another embodiment of the process of this invention is illustrated in FIG. 2. The FIG. 2 embodiment has particular utility when there is a significant amount of carbon dioxide in the feed. The numerals in FIG. 2 correspond to those of FIG. 1 plus 100 for the elements common to both. For convenience only the process differences from the FIG. 1 embodiment will be specifically described in the discussion of the FIG. 2 embodiment.

In the embodiment of FIG. 2 an additional heat exchanger 270 is incorporated for purposes of partially condensing vapor stream 228 from phase separator 201. The condensed stream 271 is reduced in pressure by passage through valve 272 and the resulting stream 273 is passed into stripping column 202. The pressure of the methane-richer fraction 263 from the low pressure column is increased to a level exceeding that of the stripping column by liquid pump 210 to allow flow of some of the fraction 263 into the stripping column. The resulting stream 264 is warmed by passage through heat exchanger 205 to form stream 265. A portion 281 of stream 265 is passed through valve 282 to form wash stream 283 which is passed into stripping column 202. The remaining portion 284 of stream 265 is expanded through valve 285 to form stream 286 which is then warmed by passage through heat exchanger 204 to form stream 287. To provide the required cooling in heat exchanger 270, portion 291 of stream 223 from phase separator 203 is passed through valve 292 to form stream 293, which is combined with stream 287 to form stream 294, which is boiled in heat exchanger 270 where it sustains the cooling of stream 228. Resulting stream 295 is warmed by passage through heat exchanger 200 to form low pressure methane product 296. Similarly nitrogen stream 254 is warmed by passage through heat exchanger 270 to form stream 258 which is further warmed by passage through heat exchanger 200 to form nitrogen product and/or waste stream 259.

An advantage of introducing stream 273 and wash liquid 283 into the stripping column is that the concentration of carbon dioxide in the feed to the double column portion of the process is reduced. This feed is the stripper overhead vapor stream 233. A lower concentration of carbon dioxide can be achieved in the overhead vapor due to washing with liquid methane, since a greater amount of methane which contains carbon dioxide is thereby removed and recovered from the stripping column. The advantage is that higher concentrations of carbon dioxide can be tolerated in the feed stream 211 without exceeding solubility limits (and therefore encountering freezing problems) in the colder portions of the process. This embodiment can handle a feed stream 211 having a carbon dioxide content of up to 10 times the amount otherwise acceptable. This serves to reduce the capital and operating costs associated with pretreatment of the feed gas.

Figure 3:
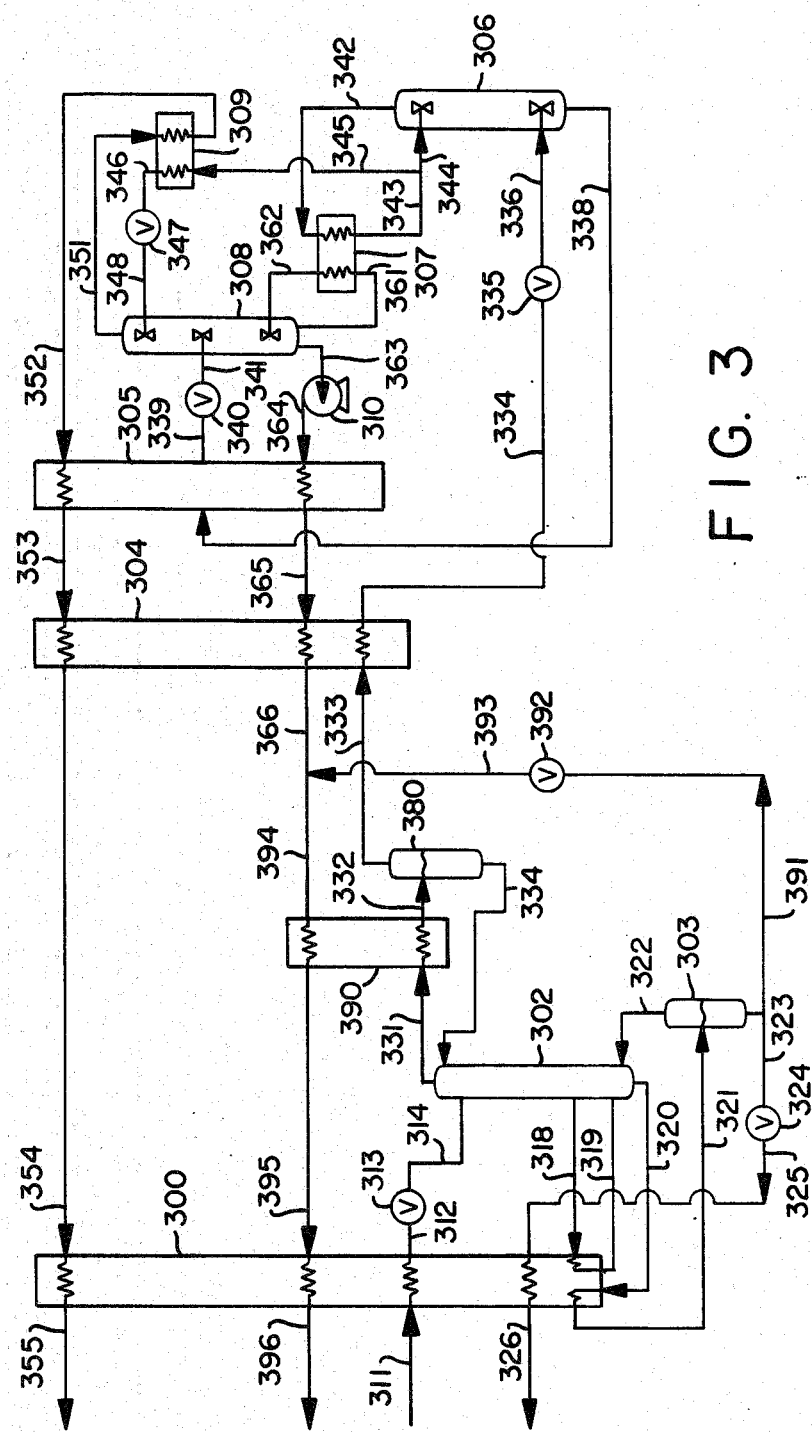
FIG. 3 is a schematic flow diagram of another preferred embodiment of the nitrogen and methane separation process of this invention wherein a top condenser is employed with the stripping column.

Another embodiment of the process of this invention is illustrated in FIG. 3. The FIG. 3 embodiment also has particular utility when there is a significant amount of carbon dioxide in the feed. The numerals in FIG. 3 correspond to those of FIG. 1 plus 200 for the elements common to both. For convenience only the process differences from the FIG. 1 embodiment will be specifically described in the discussion of the FIG. 3 embodiment.

In the embodiment of FIG. 3 the incoming feed is not phase separated but rather the entire stream 314 is introduced as feed into stripping column 302. Furthermore, a condenser 390 is added to the stripping column. Stripping column vapor 331 is partially condensed in condenser 390 and the resulting stream 332 is phase separated in phase separator 380 into stripping column top vapor 333 and liquid 334 which is returned to the stripping column as reflux. To provide the required cooling in condenser 390, portion 391 of stream 323 from phase separator 303 is passed through valve 392 to form stream 393, which is combined with stream 366 to form stream 394, which is boiled in condenser 390 where it sustains the cooling of stream 331. Resulting stream 395 is warmed by passage through heat exchanger 300 to form low pressure methane product 396.

As was the case with the FIG. 2 embodiment, an advantage of the FIG. 3 embodiment is the reduction of the carbon dioxide content of the feed stream 333 entering the double column portion of the process. This is done by removing more methane, and therefore more carbon dioxide, from the feed via the stripping column. This permits a higher concentration of carbon dioxide in the feed stream 311, before freezing problems are encountered in the colder portions of the process, with the attendant savings in pretreatment costs.

Table I lists typical process conditions obtained by a computer simulation of the process of this invention in accord with the embodiment illustrated in FIG. 1. The stream numbers correspond to those of FIG. 1. The designation psia means pounds per square inch absolute, the designation lb-moles/hr means pound moles per hour, and the designation °F. means degrees Fahrenheit.

TABLE I

| Stream No. | Flow (lb-moles/hr) | Pressure (psia) | Temp (°F.) | Composition $N_2$ | (Mole Percent) $CH_4$ |
|---|---|---|---|---|---|
| 111 | 1000 | 950 | 10 | 21 | 79 |
| 117 | 776 | 540 | −160 | 18 | 82 |
| 120 | 773 | 540 | −130 | 5 | 95 |
| 126 | 438 | 500 | −20 | 3 | 97 |
| 128 | 234 | 650 | −160 | 30 | 70 |
| 133 | 328 | 540 | −160 | 38 | 62 |
| 137 | 562 | 365 | −200 | 35 | 65 |
| 155 | 186 | 20 | −20 | 99.1 | 0.1 |
| 163 | 376 | 30 | −260 | 3 | 97 |
| 167 | 376 | 200 | −20 | 3 | 97 |

Now, by the use of the present invention, one can more efficiently separate nitrogen and methane using a double column NRU by enabling recovery of a large amount of methane at a higher pressure than that available from the NRU and by enabling the NRU to operate with higher quality reflux especially at low nitrogen concentrations. Although the invention has been described in detail with reference to three preferred embodiments, it is appreciated that there are a number of other embodiments which are within the spirit and scope of the claims.

We claim:

1. A process for the separation of nitrogen and methane employing double column cryogenic rectification in a nitrogen rejection unit comprising the recovery of methane at a pressure which exceeds that of methane as it emerges from the nitrogen rejection unit by the steps of:
   (a) introducing feed containing nitrogen and methane into a high pressure stripping column operating at a pressure in the range of from 200 to 600 psia;
   (b) passing feed down the stripping column against upflowing vapor to produce stripping column bottom liquid having a methane concentration which exceeds that of the feed, and stripping column top vapor having a nitrogen concentration which exceeds that of the feed;
   (c) partially vaporizing bottom liquid to produce nitrogen-richer vapor and methane-richer fluid;
   (d) employing the nitrogen-richer vapor in the stripping column as upflowing vapor;
   (e) passing at least some of the stripping column top vapor to a nitrogen rejection unit for separation by double column cryogenic rectification into nitrogen-richer and methane-richer fractions; and
   (f) recovering the methane-richer fluid at a pressure which exceeds that of the methane-richer fraction as it emerges from the double column nitrogen rejection unit.

2. The process of claim 1 wherein methane richer-fluid is recovered as gas.

3. The process of claim 1 wherein methane richer-fluid is recovered at a pressure which exceeds that of the methane-richer fraction, as it emerges from the nitrogen rejection unit, by at least a factor of 1.5.

4. The process of claim 1 wherein stripping column top vapor is cooled by indirect heat exchange with methane-richer and/or nitrogen-richer fractions from the nitrogen rejection unit prior to being passed to the nitrogen rejection unit.

5. The process of claim 1 wherein at least some of the methane-richer fraction from the nitrogen rejection unit is recovered as lower pressure methane.

6. The process of claim 1 wherein some of the nitrogen-richer fraction from the NRU is recovered as nitrogen gas.

7. The process of claim 1 wherein, prior to step (a), vapor containing nitrogen and methane is partially condensed and a liquid portion thereof is passed to the stripping column as feed.

8. The process of claim 7 wherein at least some of the vapor portion thereof is passed to the nitrogen rejection unit for separation into nitrogen-richer and methane-richer fractions.

9. The process of claim 8 wherein said vapor portion is combined with stripping column top vapor and the combined stream introduced into the nitrogen rejection unit.

10. The process of claim 7 wherein at least some of the vapor portion is liquified and passed into the stripping column.

11. The process of claim 10 wherein said liquefaction of the vapor portion is carried out in part by indirect heat exchange with stripping column bottom liquid.

12. The process of claim 1 wherein a portion of the methane-richer fraction from the nitrogen rejection unit is passed to the stripping column as downflow wash liquid.

13. The process of claim 1 wherein vapor is removed from the stripping column, is partially condensed, and the remaining vapor forms stripping column top vapor for passage to the nitrogen rejection unit.

14. The process of claim 13 wherein liquid from the partial condensation of the vapor removed from the stripping column is returned to the stripping column for downflow through the column.

15. The process of claim 13 wherein the partial condensation of the vapor removed from the stripping column is carried out in part by indirect heat exchange with stripping column bottom liquid.

16. The process of claim 1 wherein methane-richer fraction from the nitrogen rejection unit is increased in pressure from the pressure it has when it emerges from the nitrogen rejection unit.

17. The process of claim 1 wherein, prior to step (a), vapor containing nitrogen and methane is partially condensed, a liquid portion thereof is passed to the stripping column as feed and at least some of the vapor portion is liquefied and passed into the stripping column, and further comprising passing a portion of the methane-richer fraction from the nitrogen rejection unit to the stripping column as downflow wash liquid, whereby the concentration of carbon dioxide in the feed is reduced by a factor of up to about 10 or more, prior to its introduction as stripping column top vapor into the double column cryogenic rectification.

18. The process of claim 1 further comprising removing liquid from the stripping column, partially vaporizing said liquid by heat exchange with feed to cool the feed, and returning the resulting partially vaporized fluid to the stripping column.

* * * * *

UNITED STATES PATENT AND TRADEMARK OFFICE
CERTIFICATE OF CORRECTION

PATENT NO. : 4,664,686
DATED : May 12, 1987
INVENTOR(S) : R.F. Pahade et al

It is certified that error appears in the above-identified patent and that said Letters Patent is hereby corrected as shown below:

In column 6, line 8 delete "liguid" and insert therefor --liquid--.

Signed and Sealed this

Eleventh Day of August, 1987

Attest:

DONALD J. QUIGG

Attesting Officer

Commissioner of Patents and Trademarks